United States Patent
Peterson et al.

(10) Patent No.: US 6,280,707 B1
(45) Date of Patent: Aug. 28, 2001

(54) ORAL PROPHALAXIS PASTE

(75) Inventors: Kenneth S. Peterson, Lancaster; James M. Sherman, York; Connie Chilcott, Manchester, all of PA (US); Tse-Chong Wu, Baton Rouge, LA (US)

(73) Assignee: Dentsply International Inc., York, PA (US)

( * ) Notice: Subject to any disclaimer, the term of this patent is extended or adjusted under 35 U.S.C. 154(b) by 0 days.

(21) Appl. No.: 09/212,952

(22) Filed: Dec. 15, 1998

(51) Int. Cl.[7] ............................... A61K 7/16; A61K 31/05
(52) U.S. Cl. ........................... 424/49; 514/731; 514/734; 514/736
(58) Field of Search .................................. 514/736, 734, 514/731; 424/49

(56) References Cited

U.S. PATENT DOCUMENTS

| | | | |
|---|---|---|---|
| 3,228,845 | 1/1966 | Najjar | 167/93 |
| 4,144,322 | 3/1979 | Cordon | 424/49 |
| 4,235,874 | 11/1980 | Norfleet | 424/52 |
| 4,656,031 | 4/1987 | Lane et al. | 424/49 |
| 4,824,661 | 4/1989 | Wagner | 424/52 |
| 4,894,220 | 1/1990 | Nabi et al. | 424/52 |
| 4,980,153 | 12/1990 | Jackson et al. | 424/52 |
| 5,032,386 | 7/1991 | Gaffar et al. | 424/49 |
| 5,037,635 | 8/1991 | Nabi et al. | 424/52 |
| 5,037,637 | 8/1991 | Gaffar et al. | 424/52 |
| 5,043,154 | 8/1991 | Gaffar et al. | 424/52 |
| 5,080,887 | 1/1992 | Gaffar et al. | 424/52 |
| 5,094,845 | 3/1992 | Vlock | 424/52 |
| 5,096,701 | 3/1992 | White, Jr. et al. | 424/52 |
| 5,130,122 | 7/1992 | Tabibi et al. | 424/49 |
| 5,135,738 | 8/1992 | Gaffar et al. | 424/49 |
| 5,145,667 | 9/1992 | Ibrahim et al. | 424/52 |
| 5,156,835 | 10/1992 | Nabi et al. | 424/52 |
| 5,165,914 | 11/1992 | Vlock | 424/52 |
| 5,167,951 | 12/1992 | Gaffar et al. | 424/52 |
| 5,176,900 | 1/1993 | White, Jr. et al. | 424/52 |
| 5,178,851 | 1/1993 | Gaffar et al. | 424/52 |
| 5,180,578 | 1/1993 | Gaffar et al. | 474/52 |
| 5,188,821 | 2/1993 | Gaffar et al. | 424/52 |
| 5,188,822 | 2/1993 | Viccaro et al. | 424/52 |
| 5,192,530 | 3/1993 | Gaffar et al. | 424/52 |
| 5,192,531 | 3/1993 | Gaffar et al. | 424/52 |
| 5,192,533 | 3/1993 | Elliott et al. | 424/52 |
| 5,208,009 | 5/1993 | Gaffar et al. | 424/49 |
| 5,209,251 | 5/1993 | Curtis et al. | 132/321 |
| 5,234,688 | 8/1993 | Gaffar et al. | 424/401 |
| 5,236,696 | 8/1993 | Catiis et al. | 424/49 |
| 5,236,699 | 8/1993 | Libin | 424/54 |
| 5,256,396 | 10/1993 | Piechota, Jr. | 424/49 |
| 5,256,401 | 10/1993 | Duckenfield et al. | 424/49 |
| 5,260,062 | 11/1993 | Gaffar | 424/401 |
| 5,273,741 | 12/1993 | Gaffar et al. | 424/49 |
| 5,279,813 | 1/1994 | Gaffar et al. | 424/49 |
| 5,288,480 | 2/1994 | Gaffar et al. | 424/52 |
| 5,290,541 | 3/1994 | Liang | 424/49 |
| 5,290,542 | 3/1994 | Liang | 424/52 |
| 5,292,502 | 3/1994 | Burke et al. | 424/54 |
| 5,292,526 | 3/1994 | Gaffar et al. | 424/49 |
| 5,294,431 | 3/1994 | Gaffar et al. | 424/49 |
| 5,296,214 | 3/1994 | Gaffar | 424/49 |
| 5,312,618 | 5/1994 | Gaffar et al. | 424/52 |
| 5,316,758 | 5/1994 | Morishima et al. | 424/54 |
| 5,320,832 | 6/1994 | Catiis et al. | 424/52 |
| 5,334,375 | 8/1994 | Nabi et al. | 424/52 |
| 5,344,641 | 9/1994 | Gaffar et al. | 424/49 |
| 5,348,733 | 9/1994 | Morishima et al. | 424/52 |
| 5,354,550 | 10/1994 | Collins et al. | 424/49 |
| 5,356,615 | 10/1994 | Gaffar | 424/49 |
| 5,356,803 | 10/1994 | Carpenter et al. | 435/200 |
| 5,368,844 | 11/1994 | Gaffar et al. | 424/49 |
| 5,380,530 | 1/1995 | Hill | 424/440 |
| 5,422,098 | 6/1995 | Rolla et al. | 424/49 |
| 5,424,059 | 6/1995 | Prencipe et al. | 424/52 |
| 5,445,814 | 8/1995 | Liang | 424/52 |
| 5,453,265 | 9/1995 | Gaffar et al. | 424/52 |
| 5,466,437 | 11/1995 | Gaffar et al. | 424/52 |
| 5,472,685 | 12/1995 | Gaffar | 424/49 |
| 5,474,761 | 12/1995 | Liang | 424/52 |
| 5,496,540 | 3/1996 | Gaffar et al. | 424/49 |
| 5,500,448 | 3/1996 | Cummins et al. | 514/717 |
| 5,525,330 | 6/1996 | Gaffar et al. | 424/52 |
| 5,531,982 | 7/1996 | Gaffar et al. | 424/49 |
| 5,538,715 | 7/1996 | Gaffar et al. | 424/52 |
| 5,571,501 | 11/1996 | Toy | 424/49 |
| 5,575,652 | 11/1996 | Gaffar et al. | 433/173 |
| 5,582,816 | 12/1996 | Mandanas et al. | 424/49 |
| 5,605,676 | 2/1997 | Gaffar et al. | 424/49 |
| 5,624,906 | * 4/1997 | Vermeer | 514/23 |
| 5,639,445 | 6/1997 | Curtis et al. | 424/49 |
| 5,645,841 | 7/1997 | Hill et al. | 424/401 |
| 5,651,959 | 7/1997 | Hill et al. | 424/49 |
| 5,665,374 | 9/1997 | Hill et al. | 424/435 |
| 5,670,138 | 9/1997 | Venema et al. | 424/52 |
| 5,681,548 | 10/1997 | Esposito et al. | 424/49 |
| 5,683,678 | 11/1997 | Heckert et al. | 424/52 |

FOREIGN PATENT DOCUMENTS 0 161 899    11/1985  (EP) .
92/04884      4/1992  (WO) .

OTHER PUBLICATIONS

Remington's Pharmaceutical Sciences, 15th edition, 1975Mack Publishing Co., Chapter 105, p. 1895.*

J. Osaka Univ., Dent. Sch.; vol. 35, 5~11, 1995; "Antibacterial Effect of Composite Incorporating Triclosan against Streptococcus Mutans".

* cited by examiner

*Primary Examiner*—Shep K. Rose
*Assistant Examiner*—Donna Jagoe
(74) *Attorney, Agent, or Firm*—Douglas J. Hura; James B. Bieber

(57) ABSTRACT

An oral prophalaxis paste includes a preselected grade and amount of abrasive material such as pumice clay or diatimoceous earth. The abrasive material is moistened with water and a moisture retention agent such as glycerin is included. A curing system is employed, such as using sodium silicate and methyl salicylate. The formulation provides antimicrobial properties by the inclusion of triclosan.

3 Claims, No Drawings

ORAL PROPHALAXIS PASTE

BACKGROUND OF THE INVENTION

Oral compositions containing triclosan are known. For example, in U.S. Pat. No. 5,472,685, there is described an oral composition which includes an effective antiplaque proportion of triclosan in an oral composition. That composition is in the form of a tooth paste, gel dentrifrice, tooth powder, mouth rinse, mouth wash, tooth hardener, anticalculus composition, gum or lozenge. Such triclosan-containing compositions are known to exhibit an antibacterial effect in the oral cavity.

It has been found that the dentrifrice compositions heretofore known in the art are not useful as oral prophylaxis pastes (also referred to as "prophy" pastes). A main drawback has been that the prior dentrifrices contain low abrasive materials. This is because such dentrifrices are intended to be used on a daily basis. Therefore, prior to the present invention, there has not been a prophylaxis paste which exhibits antimicrobial properties and which is abrasive enough to be employed by the dental practitioner as a prophalaxis paste.

Therefore, a need exhibits for a prophy paste with acceptable abrasive qualities as well as antimicrobial qualities. The present invention, as will be discussed below meets this need.

DISCLOSURE OF THE INVENTION

It is therefore, an object of the invention to provide an oral prophylaxis paste.

It is another object of the invention to provide a prophylaxis paste with useful abrasive qualities.

It is a further object of the invention to provide such a prophylaxis paste which also exhibits antimicrobial properties.

These and other objects of the invention which will become apparent from the description to follow are accomplished by the invention as hereinafter described and claimed.

In general, a prophylaxis paste comprises a preselected amount and grade of pumice, clay, glycerin and an amount of triclosan.

PREFERRED EMBODIMENTS FOR CARRYING OUT THE INVENTION

The dental prophalaxis paste composition according to the invention is based upon a moistened pumice baseor clay base, normally containing an amount of pumice or clay, water and preferably a moisture retention agent in the form of glycerin.

The novel paste has a pumice base or clay base moistened to a pasty state. The exact amount of moisture added may be varied within reasonable limits because changing the moisture content in small amounts, although altering the paste consistency does not materially alter the characteristics which depend on the addition of further components. It has been found that the moisture retention agent may also be varied within reasonable amounts because its presence within a limited range does not significantly alter the desired flowing and non-splattering characteristics desired in the paste.

It is preferred to add glycerin and water to the pumice base in a weight amount ratio of about 16:8:4 of pumice or clay, glycerin and water. However, as indicated, the glycerin may readily range from about 6–9 parts to 16 parts of pumice, while the water can vary between about 4 to 6 parts per 16 parts of base without significantly altering the characteristics of the paste.

It will be readily understood that various substitutes for the preferred glycerin as the moisture retention agent could conceivably be made. Glycerin has been found to work effectively without detracting from the desired final qualities of the paste.

It is envisioned that a prophalaxis paste according to the present invention will be prepared as a fine, medium or coarse grit compound. These designations are relative, and are not necessarily intended to convey exact grades or grit levels. However, preferred explary compositions will be discussed below. The pumice or clay grade used in each of the different grit pastes is based upon the average particle size of the respective pumice. The table given below provides a grade designation and the average particle size in mesh, inches and microns.

| PUMICE CLASSIFICATIONS | | | |
|---|---|---|---|
| PUMICE GRADE | MESH SPEC | INCH, MM | UM |
| 4F | 170 100% T | .0035, .090 | 90 |
|  | 200 99% T | .0029, .075 | 75 |
|  | 325 85% T | .0017, .045 | 45 |
| 3F | 170 <1% R | .0035, .090 | 90 |
|  | 200 <8% R | .0029, .075 | 75 |
| 2F | 140 <2% R | .0041, .106 | 106 |
|  | 170 <9% R | .0035, .090 | 90 |
|  | 200 80–99% T | .0029, .075 | 75 |
| 1F | 100 <1% R | .0059, .150 | 150 |
|  | 120 <7% R | .0049, .125 | 125 |
|  | 200 60–90% T | .0029, .075 | 75 |
| 0 | 80 <2% R | .0070, .180 | 180 |
|  | 100 <10% R | .0059, .150 | 150 |
|  | 200 40–80% T | .0029, .075 | 75 |

NOTE 1: T = Passes through the sieve, R = Remains on sieve

A fine grit prophalaxis paste according to the invention will include about 40–50 percent by weight of pumice grade 4F. A medium grit paste will include from about 10–15% of pumice grade 3F and 35–40% of grade 2F. A coarse grit composition will contain for example, 35–40% by weight of pumice grade 2F and 10–15% of pumice grade 0. It is envisioned that other composition containing different grit levels are within the scope of the present invention. For example, a more coarse composition might include 35–40% of pumice grade 1F and 10–15% by weight of pumice grade 0. Again, other amounts of pumice or combinations of pumice may fall within a given designation, without varying from the scope of the present invention. Again, the designations fine, medium and coarse are relative and subjective.

With this understanding, fine, medium and coarse grit level compositions according to the invention may contain the following components.

TABLE 1

| | Grit Levels | | |
|---|---|---|---|
| Ingredient Name | (% w/w) Fine | Medium | Coarse |
| Purified Water | QS | QS | QS |
| Pumice 2F | — | 36.60 | 37.57 |
| Pumice 3F | — | 12.60 | — |
| Pumice 4F | 45.20 | — | — |

TABLE 1-continued

| Ingredient Name | (% w/w) Fine | Grit Levels Medium | Coarse |
|---|---|---|---|
| Pumice O | — | — | 12.94 |
| Dacalite | 4.00 | — | — |
| Glycerin | 29.80 | 30.77 | 30.06 |
| Polyethylene Glycol 400 | 1.00 | 1.00 | 1.00 |
| Triclosan | 0.3–1.0 | 0.3–1.0 | 0.3–1.0 |
| Sodium Fluoride | 2.70 | 2.70 | 2.70 |
| Sodium Silicate | 2.86 | 2.86 | 2.63 |
| Monosodium Phosphate | 0.15 | 0.15 | 0.16 |
| Methyl Salicylate | 0.85 | 0.85 | 0.81 |
| Sodium Saccharin | 0.04 | 0.04 | 0.04 |
| Sodium Carboxymethylcellulose | 0.05 | 0.05 | 0.05 |
| Colorant Solution | 0.15 | 0.15 | 0.10 |
| Flavor | 0.82 | 0.83 | 0.81 |
| TOTAL, % | 100.00 | 100.00 | 100.00 |

Alternative compositions within the scope of the invention are provided in Table 2.

TABLE 2

| Ingredient Name | (% w/w) Fine | Medium | Coarse |
|---|---|---|---|
| Purified Water | 13.237 | 11.222 | 10.948 |
| Pumice | 45.20 | 49.21 | 50.51 |
| Glycerin | 28.70 | 30.77 | 30.00 |
| Distomacsous Earth | 4.00 | — | — |
| Sodium Fluoride | 2.78 | 2.70 | 2.73 |
| Sodium Silicate | 2.86 | 2.86 | 2.63 |
| Polyethylene Glycol 400 | 1.00 | 1.00 | 1.00 |
| Methyl Sallcylate | 0.85 | 0.85 | 0.81 |
| Flavorant | 0.82 | 0.83 | 0.81 |
| Triclosan | 0.82 | 0.83 | 0.81 |
| Sodium Phosphate Monobasic | 0.15 | 0.15 | 0.16 |
| Monosodium Phosphate | 0.15 | 0.15 | 0.16 |
| Sodium Saccharin | 0.04 | 0.04 | 0.04 |
| Sodium Carboxymethyl Cellulose | 0.05 | 0.05 | 0.05 |
| FD&C Blue #1 | — | 0.009 | — |
| FD&C Blue #2 | — | 0.009 | — |
| FD&C Blue #6 | 0.013 | — | — |
| FD&C Blue #40 | — | — | 0.012 |
| TOTAL, % | 100.00 | 100.00 | 100.00 |

To the pumice paste, containing pumice, glycerin and water, as discussed above, is added the sodium silicate, methyl salicylate and sodium carboxymethycellulose. The sodium silicate and methyl salicylate together form the curing system of the composition in the ratios of sodium silicate (3–4 parts) to methyl salicylate (0.25–1.25 parts). The sodium carboxymethylcellulose acts as a gum. Other materials may be included as a gum such as agar agar or the like. It has been found that these materials, when employed in the paste, act synergistically to create unique flow characteristics in the paste. By blending an amount of a gum system, such as sodium carboxymethylcellulose, and a small amount of the curing system, that is up to about 2% by weight of the gum system and up to about 10% by weight of the cure system, the material will flow smoothly under pressure, without segregation or settling of the pumice.

Dacalite is also a useful grit material, as is diatomaceous earth. The polyethylene glycol is also a moisture retaining agent; sodium fluoride is known to be used as an anticarries agent; monosodium phosphate is a buffer; and sodium saccharin is added as a sweetener. Colorant solutions and flavoring agents are optional as are the sweetener and the sodium fluoride.

An example of the prophalaxis paste without the triclosan is provided in U.S. Pat. No. 3,228,845, which is hereby incorporated by reference for such disclosure. It has been found that the addition of the antimicrobial agent of triclosan in an amount of from 0.2 to about 1.2 percent by weight provides a dental prophalaxis paste with desirable antimicrobial properties.

The prophalaxis paste according to the present invention have abrasion values above those of the dentrifices currently known commercially. The abrasive ratings table provided below gives an example of the inventive prophy pastes and their relative dental abrasion (RDA) values as compared to commercially available dentrifices.

| Products | Dentin Abrasion (RDA) Values |
|---|---|
| Inventive Paste Fine Grit | 704 |
| Inventive Paste Medium Grit | 256 |
| Inventive Paste Coarse Grit | 362 |
| Crest Regular Toothpaste | 81 |
| Crest Tartar Control Toothpaste | 126 |
| Colgate Tartar Control Toothpaste | 112 |
| Aim Tartar Control Toothpaste | 127 |
| Aquafresh Tartar Control Toothpaste | 125 |
| Close-up Tartar Control Toothpaste | 120 |

The RDA value as used in the present description, may be determined by any of the standard methods including the Grabensteder method or the Hefferen method. The Hefferen method is preferred because it is recognized by the American Dental Association. While the RDA is the method for evaluation the abrasive nature of normally, toothpaste, another method known as the relative enamel abrasion (REA) is normally used for evaluating prophy paste. There is no specific correlation between the recognized RDA and REA test methods. According to the present invention, a prophy paste having a REA value of preferably above about 3 is within the scope of the invention.

GENERAL EXPERIMENTAL

In order to demonstrate the effectiveness of the present invention in carrying out the objects as set forth above, a number of formulations were prepared according to the present invention. Medium, fine and coarse grit formulations were prepared. Samples 1 and 2 contain medium grit pumice and 0.3% and 1.0% triclosan respectively. Sample 3 is a medium grit prophy paste available from DENTSPLY International Inc. As NUPRO. Samples 4 and 5 contain fine grit and 0.3% and 1.0% triclosan respectively. Sample 6 is a fine grit NUPRO prophy paste. Samples 7 and 8 are a coarse grit, 0.3% and 1.0% triclosan respectively formulation. Sample 9 is a coarse grit NUPRO prophy paste. The NUPRO prophy paste as used in these experiments are commercially available.

PROCEDURE

Culture Preparation

*Klebsiella pneumoniae* and *Streptococcus mutans* were used in the assay. The cultures were maintained lyophilized prior to use. *Klebsiella pnumoniae* was grown on soybean casein digest agar (LMRS) at 37±2° C. for 18–24 hours. Streptococcus was grown on soybean casein digest agar with 5% blood (BAP) at 37±2° C. for 48–72 hours. The cultures were harvested in 0.9% saline to the approximate turbidity of a 0.5 McFarland standard.

Test Performance

The Klebsiella suspension was added to Mueller Hinton agar and the Streptococcus suspension was added to BAP with sterile cotton swabs using a three direction sweep (Kirby-Bauer method). Six plates were prepared for each organism.

The products were added to sterile ¼ inch filter paper discs using 10 mg per disc. Twelve discs were prepared for each product.

The discs were added to the inoculated plates. One disc containing each product on each plate. The Klebsiella plates were incubated at 37±2° C. for 18–24 hours. The Streptococcus plates were incubated at 37±2° C. for 48 hours. The diameters of the zones of inhibition were then measured for each product using a caliper.

RESULTS

Table 2 contains the results for the products against *Klebsiella pneumoniae*. Table 3 contains the results for the products against Streptococcus mutans. The tables also contain the average diameter of the zones of inhibition for each product against each organisms. The average zone of inhibition was calculated from six replicates. The products with a 0 mm zone diameter demonstrated inhibition directly under the sample only (no diffusion of antimicrobial activity).

The sample that showed the largest zone of inhibition against *Klebsiella pneumoniae* was Sample 5. The sample that showed the largest zone of inhibition against *Streptoccocus mutans* was Sample 8.

TABLE 2

| Sample ID | Average Zone Diameter |
| --- | --- |
| 1 | 37.6 mm |
| 2 | 40.0 mm |
| 3 | 0 mm |
| 4 | 38.6 mm |
| 5 | 41.6 mm |
| 6 | 0 mm |
| 7 | 36.5 mm |
| 8 | 38.5 mm |
| 9 | 0 mm |

TABLE 3

| Sample ID | Average Zone Diameter |
| --- | --- |
| 1 | 10.1 mm |
| 2 | 10.9 mm |
| 3 | 0 mm |
| 4 | 10.1 mm |
| 5 | 11.1 mm |
| 6 | 0 mm |
| 7 | 9.6 mm |
| 8 | 12.8 mm |
| 9 | 0 mm |

Therefore, it is apparent that a prophalaxis paste according to the invention as described above, is useful in meeting the stated objectives of the invention. It will be understood that amount of various components, can be varied and still fall within the scope of the invention. Similarly, specific formulation components as provided above are merely explary, and other components similar or otherwise are also within the scope of the invention. The scope of the invention will be determined only by the claims.

What is claimed is:

1. A dental prophylactic paste comprising a composition having a paste component and an antimicrobial component, wherein the prophylactic paste has a relative dental abrasion value of above 200, wherein said antimicrobial component comprises 2,2,4'-trichloro-2'-hydroxydiphenyl ether, and wherein said composition comprises from about 99.8 percent by weight of said paste component and from about 0.2 to about 1.2 percent by weight of said antimicrobial component, and wherein said paste component comprises a weight ratio of (a) about 16 parts of a dental abrasive selected from the group consisting of pumice, clay and mixtures thereof, to (b) about 6 to about 16 parts of a moisture retention agent, to (c) about 4 to about 6 part of water.

2. A dental prophylactic paste as in claim 1, wherein said moisture retention agent is glycerin.

3. A dental prophylactic paste as in claim 1, having a relative enamel abrasive value of above about 3.

* * * * *

UNITED STATES PATENT AND TRADEMARK OFFICE
CERTIFICATE OF CORRECTION

PATENT NO.    : 6,280,707 B1
DATED         : August 28, 2001
INVENTOR(S)   : Kenneth S. Peterson, James Sherman and Connie Chilcott It is certified that error appears in the above-identified patent and that said Letters Patent is hereby corrected as shown below:

<u>Title page,</u>
Item [75], Inventors, delete inventor "Tse-Chong Wu"

Signed and Sealed this

Thirtieth Day of July, 2002

Attest:

JAMES E. ROGAN
Attesting Officer    Director of the United States Patent and Trademark Office